United States Patent
DeVore et al.

[11] Patent Number: 6,063,082
[45] Date of Patent: May 16, 2000

[54] PERCUTANEOUS MYOCARDIAL REVASCULARIZATION BASKET DELIVERY SYSTEM AND RADIOFREQUENCY THERAPEUTIC DEVICE

[75] Inventors: Lauri DeVore, Seattle, Wash.; Louis Ellis, St. Anthony, Minn.; Gary L. Hendrickson, Big Lake, Minn.; Daniel M. Lafontaine, Plymouth, Minn.; Zihong Guo, Bellevue; Ryan Kaveckis, Seattle, both of Wash.

[73] Assignee: SciMed Life Systems, Inc., Maple Grove, Minn.

[21] Appl. No.: 09/035,738

[22] Filed: Mar. 5, 1998

Related U.S. Application Data

[60] Provisional application No. 60/064,210, Nov. 4, 1997.

[51] Int. Cl.$^7$ .................................................. A61B 18/14
[52] U.S. Cl. ............................ 606/45; 606/47; 606/48; 606/170; 606/186
[58] Field of Search ............................ 606/41, 45, 47, 606/48, 167, 170, 186; 607/99, 122

[56] References Cited

U.S. PATENT DOCUMENTS

| | | | |
|---|---|---|---|
| 4,660,571 | 4/1987 | Hess et al. | 128/784 |
| 4,790,311 | 12/1988 | Ruiz | 128/303.1 |

(List continued on next page.)

FOREIGN PATENT DOCUMENTS

| | | | |
|---|---|---|---|
| 2560052 | 8/1985 | France | 606/41 |
| 296 09 350 U1 | 10/1996 | Germany | |
| 195 37 084 A 1 | 4/1997 | Germany | |
| WO 96/35469 | 11/1996 | WIPO | |
| WO 96/39963 | 12/1996 | WIPO | |
| WO 97/17892 | 5/1997 | WIPO | |
| WO 97/18768 | 5/1997 | WIPO | |
| WO 97/29803 | 8/1997 | WIPO | |
| WO 97/32551 | 9/1997 | WIPO | |
| WO 97/44071 | 11/1997 | WIPO | |

OTHER PUBLICATIONS

Mirhoseini et al., Abstract entitled "Transventricular Revascularization by Laser", *Lasers in Sugery and Medicine*, 2(2), 1982, 1 p.

Gal et al., Abstract entitled "Analysis of Photoproducts Free Radicals and Particulate Debris Generated . . . ", *Lasers in Surgery and Medicine*, 11(2) 1991, 1 p.

Isner, J., Abstract entitled "Right Ventricular Myocardial Infarction", *JAMA*, v259, n5, Feb. 5, 1988, 12 pp.

Pickering et al., Abstract entitled "Proliferative Activity in Peripheral and Coronary Atherosclerotic Plaque . . . ", *J. Clin. Invest.*, ISSN 0021-9738, Apr. 1993, 1 p.

(List continued on next page.)

*Primary Examiner*—Lee Cohen
*Attorney, Agent, or Firm*—Crompton, Seager & Tufte, LLC

[57] ABSTRACT

An intravascular device and methods for forming multiple percutaneous myocardial revascularization (PMR) holes in a heart chamber wall simultaneously. One device includes a basket formed of flexible arms carrying cutting probes over their length. The basket arms are outwardly arcuately biased so as to assume an outwardly bowed, arcuate shape when unconstrained. The device includes an inner shaft distally secured to a proximal portion of the basket and slidably disposed within an outer shaft. The inner shaft and collapsed basket can be retracted within the outer shaft, delivered intravascularly to the left ventricle, and distally advanced, forcing the basket to assume the bowed shape. Radio frequency current supplied to the electrical cutting probes burn holes into the ventricle wall and myocardium. One embodiment has high pressure fluid jet cutting means. Another embodiment uses a basket as an anchor to position a steerable cutting probe. Yet another embodiment includes a brush formed of multiple, arcuate, outwardly splayed electrodes that can contact heart chamber walls once advanced distally from a constraining outer shaft.

22 Claims, 5 Drawing Sheets

U.S. PATENT DOCUMENTS

| | | | |
|---|---|---|---|
| 4,896,671 | 1/1990 | Cunningham et al. | 128/642 |
| 5,047,026 | 9/1991 | Rydell | 606/48 |
| 5,093,877 | 3/1992 | Aita et al. | 385/34 |
| 5,358,485 | 10/1994 | Vance et al. | 604/22 |
| 5,364,393 | 11/1994 | Auth et al. | 606/34 |
| 5,370,675 | 12/1994 | Edwards et al. | 607/101 |
| 5,380,316 | 1/1995 | Aita et al. | 606/7 |
| 5,389,096 | 2/1995 | Aita et al. | 606/15 |
| 5,403,311 | 4/1995 | Abele et al. | 606/49 |
| 5,437,665 | 8/1995 | Munro | 606/47 |
| 5,454,782 | 10/1995 | Perkins | 604/20 |
| 5,471,982 | 12/1995 | Edwards et al. | 128/642 |
| 5,522,815 | 6/1996 | Durgin, Jr. et al. | 606/50 |
| 5,558,073 | 9/1996 | Pomeranz et al. | 128/642 |
| 5,591,159 | 1/1997 | Taheri | 606/15 |
| 5,593,405 | 1/1997 | Osypka | 606/15 |
| 5,607,405 | 3/1997 | Decker et al. | 604/264 |
| 5,620,414 | 4/1997 | Campbell, Jr. | 604/22 |
| 5,672,174 | 9/1997 | Gough et al. | 606/41 |
| 5,681,308 | 10/1997 | Edwards et al. | 606/41 |
| 5,683,366 | 11/1997 | Eggers et al. | 604/114 |
| 5,697,882 | 12/1997 | Eggers et al. | 604/114 |
| 5,700,259 | 12/1997 | Negus et al. | 606/14 |
| 5,713,894 | 2/1998 | Murphy-Chutorian et al. | 606/15 |
| 5,725,521 | 3/1998 | Mueller | 606/7 |
| 5,725,523 | 3/1998 | Mueller | 606/15 |
| 5,807,392 | 9/1998 | Eggers | 606/31 |
| 5,827,276 | 10/1998 | LeVeen et al. | 607/99 |
| 5,830,210 | 11/1998 | Rudko et al. | 607/99 |
| 5,836,947 | 11/1998 | Fleischman et al. | 606/47 |

OTHER PUBLICATIONS

Vineberg et al., "Creation of Intramyocardial Pathways to Channel Oxygenated Blood Between Ventricular Arteriolar Zones", *Canad. Med. Ass. J.*, vol. 96, Feb. 4, 1967, 3 pp.

Vineberg, A., "Results of 14 Years' Experience in the Surgical Treatment of Human Coronary Artery Insufficiency", *Canad. Med. Ass. J.*, vol. 92, Feb. 13, 1965, 8 p.

Vineberg et al., "The Ivalon Sponge Procedure for Myocardial Revascularization", *Surgery*, vol. 47, No. 2, Feb. 1960, pp. 268–289.

Vineberg et al., "Treatment of Acute Myocardial Infarction by Endocardial Resection", *Surgery*, vol. 57, No. 6, Jun. 1965, pp. 832–835.

Walter et al., "Treatment of Acute Myocardial Infarction by Transmural Blood Suply from the Ventricular Cavity",*European Surgical Research*, 3:130–138 (1971).

Khazei et al., "Myocardial Canalization", *The Annals of Thoracic Surgery*, vol. 6, No. 2, Aug. 1968, pp. 163–171.

Hershey et al., "Transmyocardial Puncture Revascularization", *Geriatrics*, Mar. 1969, pp. 101–108.

Press Release dated Oct. 21, 1996, "Doctor's Demonstrate Proof of Blood Flow Through Open TMR Channels Created with PLC Systems . . . ", 1 p.

Press/News Release dated Oct. 10, 1996, "Texas Fieart Institute Presents Study Comparing the Use of CO2 . . .", 1 p.

Goldman et al., "Nonoperative Portacaval Shunt in Swine", *Investigative Radiology*, vol. 25, No. 5, May 1990, 5 pp.

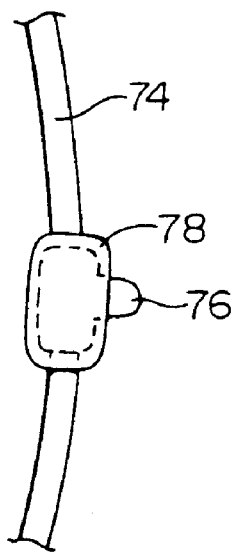
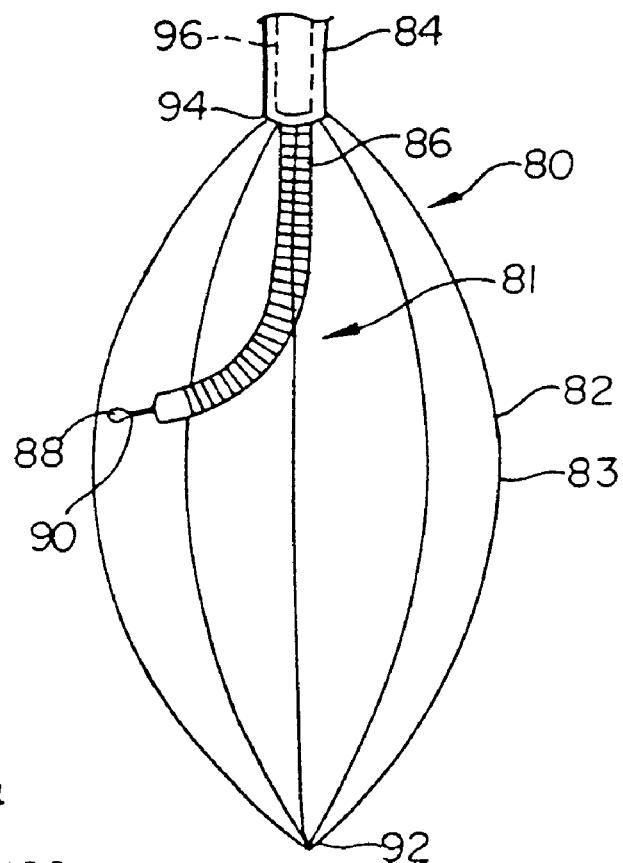
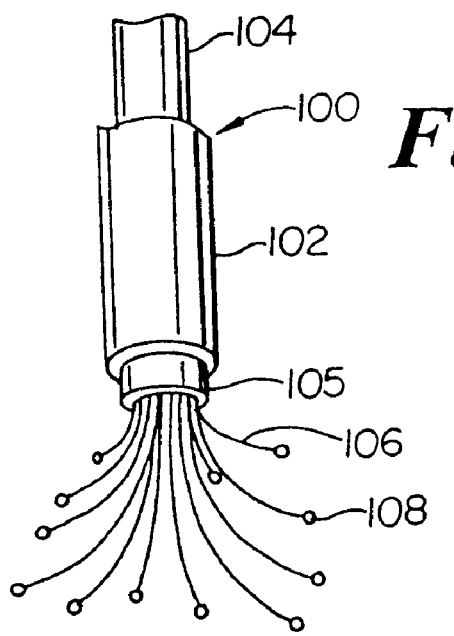
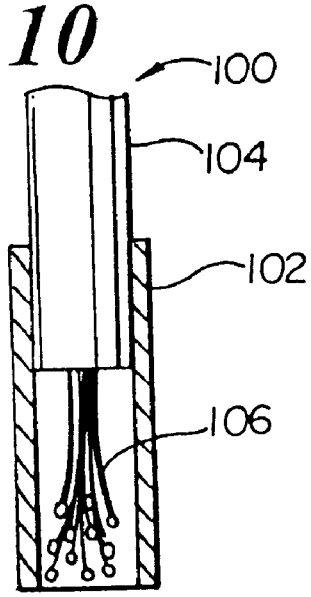

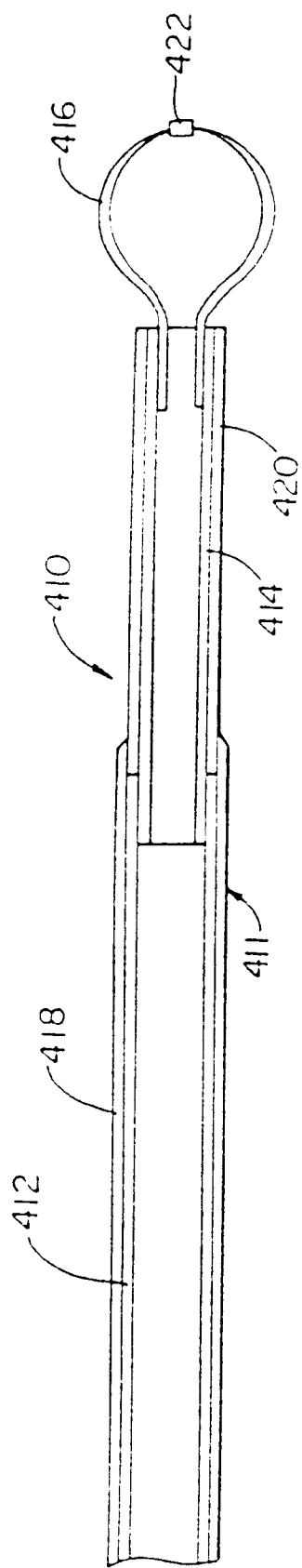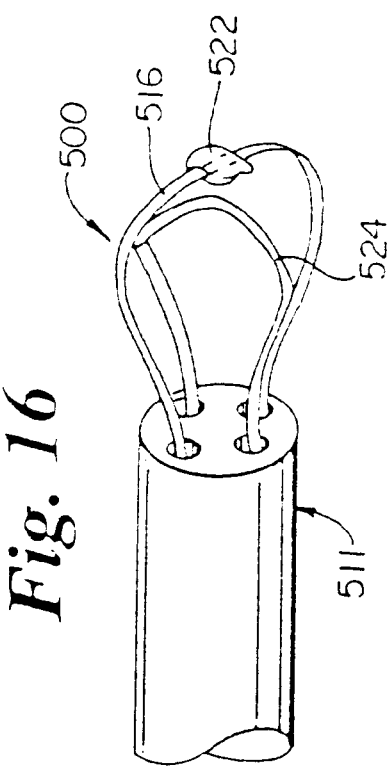

6,063,082

PERCUTANEOUS MYOCARDIAL REVASCULARIZATION BASKET DELIVERY SYSTEM AND RADIOFREQUENCY THERAPEUTIC DEVICE

RELATED APPLICATIONS

The present application is related to U.S. Provisional Patent Application Serial No. 60/064,210, filed Nov. 4, 1997, and entitled TRANSMYOCARDIAL REVASCULARIZATION GROWTH FACTOR MEDIUMS AND METHOD. The present application is also related to U.S. patent application Ser. No. 08/812,425, filed on Mar. 6, 1997, now U.S. Pat. No. 5,968,059, entitled TRANSMYOCARDIAL REVASCULARIZATION CATHETER AND METHOD and U.S. patent application Ser. No. 08/810.830, filed Mar. 6, 1997, now U.S. Pat. No. 5,938,632, entitled RADIOFREQUENCY TRANSMYOCARDIAL REVASCULARIZATION APPARATUS AND METHOD, herein incorporated by reference.

FIELD OF THE INVENTION

The present invention relates generally to medical devices for forming holes in heart chamber interior walls in percutaneous myocardial revascularization (PMR) procedures. More specifically, the present invention relates to intravascular PMR devices having expandable baskets deployable within heart chambers.

BACKGROUND OF THE INVENTION

A number of techniques are available for treating cardiovascular disease such as cardiovascular by-pass surgery, coronary angioplasty, laser angioplasty and atherectomy. These techniques are generally applied to by-pass or open lesions in coronary vessels to restore and increase blood flow to the heart muscle. In some patients, the number of lesions are so great, or the location so remote in the patient vasculature that restoring blood flow to the heart muscle is difficult. Percutaneous myocardial revascularization (PMR) has been developed as an alternative to these techniques which are directed at by-passing or removing lesions.

Heart muscle may be classified as healthy, hibernating and "dead". Dead tissue is not dead but is scarred, not contracting, and no longer capable of contracting even if it were supplied adequately with blood. Hibernating tissue is not contracting muscle tissue but is capable of contracting, should it be adequately re-supplied with blood. PMR is performed by boring channels directly into the myocardium of the heart.

PMR was inspired in part by observations that reptilian hearts muscle is supplied primarily by blood perfusing directly from within heart chambers to the heart muscle. This contrasts with the human heart, which is supplied by coronary vessels receiving blood from the aorta. Positive results have been demonstrated in some human patients receiving PMR treatments. These results are believed to be caused in part by blood flowing from within a heart chamber through patent channels formed by PMR to the myocardial tissue. Suitable PMR holes have been burned by laser, cut by mechanical means, and burned by radio frequency current devices. Increased blood flow to the myocardium is also believed to be caused in part by the healing response to wound formation. Specifically, the formation of new blood vessels is believed to occur in response to the newly created wound.

What would be desirable is a device capable of forming multiple holes in the wall of a heart chamber but requiring minimal manipulation while positioned within the chamber. What would be desirable is a device capable of forming multiple holes in a short time period in the myocardium.

SUMMARY OF THE INVENTION

The present invention provides devices and methods for forming a plurality of holes in a heart chamber wall as part of a percutaneous myocardial revascularization (PMR) treatment. Devices according to the present invention have a basket, termed a PMR basket, formed of a plurality of arcuately biased flexible arms. The arms can assume an outwardly bowed configuration once freed of the confines of a shaft lumen. The fully deployed PMR basket arms can expand until the arms engage the walls of the heart chamber. Some devices provide for multiple, simultaneous myocardial hole formation. In such devices, cutting means such as RF electrodes are carried on the arms and disposed outwardly to engage the heart chamber walls. The term "cutting" as used herein, means penetration, including the formation of holes by burning and by other means. One device utilizes a PMR basket to anchor or stabilize a steerable PMR cutting probe within the heart chamber.

The present invention provides devices and methods for forming numerous holes in a heart chamber wall within a short time period. This reduces the amount of time the heart chamber is invaded by the foreign device. Some devices and methods according to the present invention allow for the formation of many holes while requiring minimal maneuvering once the devices are advanced into the heart chamber.

One group of PMR basket devices includes an elongate outer tubular shaft having a lumen, a proximal end and a distal end. A plurality of elongate flexible arms are secured together at their proximal and distal ends, the arms being biased so as to bow outward relative to an axis through the secured proximal and distal ends. The arms carry a plurality of cutting means disposed in an outward direction toward the chamber wall. One device arms have lumens therethrough and outwardly oriented apertures. This device includes electrical supply wires running though the arms lumens and electrode wires extending from the supply wires and through the arm apertures. This device can include arcuately biased electrode wires that can be formed of a shape memory material. The biased arms can extend radially outward away from the arm when unconstrained, especially when heated by body fluids. One device includes a single supply wire slidably disposed within the arm lumen and electrically connected to each of the electrode wires which are slidably disposed within an arm aperture. The electrode wires can be advanced away from the apertures by advancing the supply wire within the arm. A variation of this embodiment utilizes cutting probes having sharpened free ends capable of piercing the heart chamber wall and forming holes within the myocardium.

In another embodiment of the PMR basket, the basket includes a plurality of electrode groupings. The electrodes can also have a loop shape, which can be, for example, semi-circular. Both the electrode grouping and loop shaped electrodes can be used to form craters in the myocardium of a patient's heart rather than channels. Craters can be considered wounds which have a width greater than their depth, whereas channels can be considered to a have a depth greater than their width. A hole is the resulting space after volumetric removal of material has been made from the patient's heart wall. A hole can be either a crater or a channel. It is believed that forming craters, in some instances, provide better therapeutic value than forming channels in the myocardium as their formation can be better controlled to reduce the likelihood of heart wall perforation.

BRIEF DESCRIPTION OF THE DRAWINGS

FIG. 7 is fragmentary, side view of a PMR basket arm having an insulated, electrical cutting probe;

FIG. 8 is a fragmentary, perspective view of a PMR basket anchor and steerable PMR cutting probe disposed within the basket;

FIG. 9 is a fragmentary, perspective view of a PMR brush device having a plurality of arcuately biased electrical cutting probes, the device being in an expanded state;

FIG. 10 is a fragmentary, side, cutaway view of the PMR brush device of FIG. 9 in a retracted, compact state;

DETAILED DESCRIPTION OF THE PREFERRED EMBODIMENTS

Figure 1:
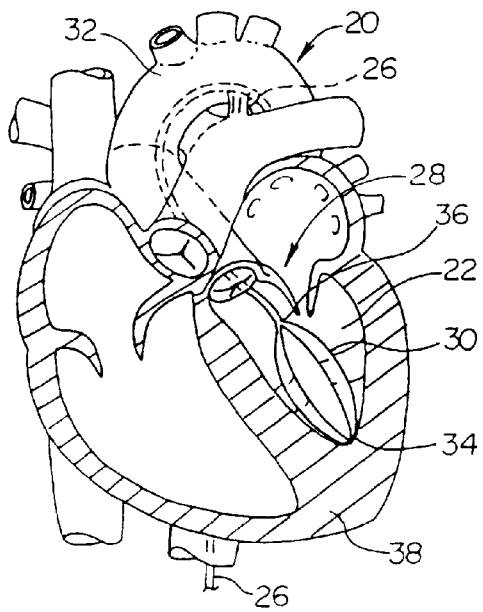
FIG. 1 is a perspective, cutaway view of a human heart having a PMR basket device inserted over the aorta and into the left ventricle.

Referring to FIG. 1, a human heart 22, including an apex 38, a left ventricle 22 and an aorta 32, is illustrated having a PMR basket device 28 disposed within ventricle 22. PMR basket device 28 includes an elongate outer shaft 26 lying within aorta 32 and a basket 30 disposed within left ventricle 22. PMR basket 30 includes a distal portion 34 and a proximal portion 36, with distal portion 34 disposed near apex 38.

Figure 2:
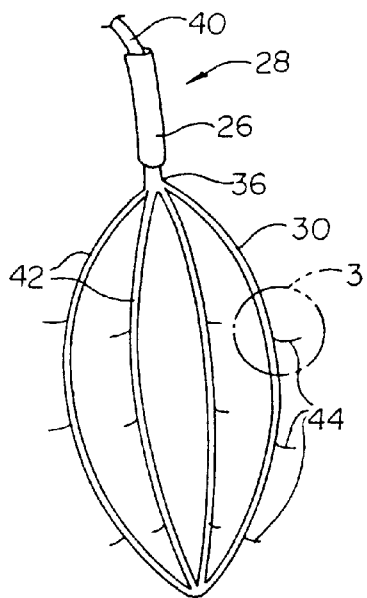
FIG. 2 is a fragmentary, perspective view of the PMR basket device of FIG. 1, having cutting probes and flexible arms in an expanded state.

Referring now to FIG. 2, PMR device 28 is illustrated in more detail, having an inner shaft 40 slidably disposed within outer shaft 26. PMR basket 30 includes a plurality of flexible arms 42 secured together at distal portion 34 and proximal portion 36. In one embodiment, PMR device 28 is constructed in a similar manner to the electrophysiological mapping device disclosed in U.S. Pat. No. 5,628,313 (Webster, Jr.), herein incorporated by reference. In particular, the construction of arms 42, shafts 26 and 40, and their interconnections can be similar. Flexible arms 42 include several cutting probes 44 depicted generally in FIG. 2. In a preferred embodiment, cutting probes 44 have a length "L" extending from flexible arms 42 that decreases with increasing distal distance along the device. Thus, in a preferred embodiment, the length of cutting probes 44 is least near distal portion 34. A shorter cutting probe length is desirable as the heart wall is generally thinner near the apex. As can be appreciated, the basket might also be used as a probe to map conductive versus non-conductive myocardial tissue.

As can be seen from inspection of FIG. 2, proximally retracting inner shaft 40 within outer shaft 26 will result in arms 42 being proximally withdrawn into outer shaft 26, thereby collapsing basket 30. Conversely, distally advancing inner shaft 40 results in arms 42 being distally advanced as well, freeing arms 42 from the constraint of shaft 26. Arms 42 have an arcuate outward bias as illustrated in FIG. 2. The arcuate bias allows arms 42 to expand and form basket 30 once freed from the confines of outer shaft 26. Arms 42 are preferably formed of a shape memory material such as Nitinol, which can assist in the formation of expanded basket 30, as arms 42 re-attain an outwardly bowed, arcuate shape. As can be seen from inspection of FIG. 1, basket 30 can be further expanded by distally forcing inner shaft 40 against basket proximal portion 36, thereby pushing basket distal portion 34 against the ventricle wall and forcing arms 42 even further apart. The longitudinally directed force of inner shaft 40 is thus partially transmitted into radially directed forces over cutting probes 44. In embodiments where the cutting probes are sharpened needles, the radial force can operate to force the needles into the heart chamber wall. In embodiments where cutting probes are electrical, the radial force can operate to bring the cutting probes into sufficiently close proximity to the heart chamber wall to allow burning holes into the heart chamber wall and myocardium.

In one embodiment, cutting probes 44 are formed of Nitinol or other shape memory material and have a bias or preform of their own. One bias is an arcuate bias as illustrated in FIG. 2. Cutting probes in this embodiment lie flat against arms 42 while the arms are retracted within outer shaft 26 and are allowed to assume a remembered, arcuate shape upon release from the constraint of outer shaft 26 and exposure to warm body fluids. Once in the arcuate position, cutting probes 44 are better able to contact the ventricle walls. In another embodiment, not requiring illustration, the cutting probes are formed of Nitinol and wound into a tight spiral which extends and lengthens the spiral into a less tightly wound spiral or straighter wire upon assuming the remember shape. The spiral wound embodiment also allows the cutting arms to extend to the ventricle walls.

Figure 3:
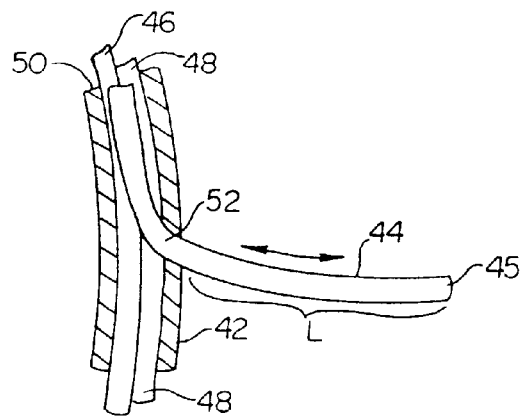
FIG. 3 is an expanded, cutaway view of detail area 3 of FIG. 2, having a PMR basket cutting probe slidably disposed within an arm.

Referring now to FIG. 3, an enlargement of cutting probe 44 illustrates an extensible length "L", extending radially from the generally longitudinal orientation of arm 42. Cutting probe 44 terminates in a cutting tip 45. In a preferred embodiment, cutting probe 44 is an electrode and cutting tip 45 cuts into the ventricle wall due to the application of an electrical signal, preferably a radio frequency (RF) current, to the ventricle walls. A lumen 50 in arm 42 contains a first supply wire 46 which is bonded to, and electrically connected to, cutting probe 44. In the embodiment illustrated, a second supply wire 48 also extends through arm 42, for interconnection to a cutting probe. In one embodiment, more than one supply wire runs within arm lumen 50. In one lumen, a unique supply wire can exist for every electrode wire. In a preferred embodiment, a single supply wire runs within each arm and is electrically connected to multiple electrode wire cutting probes. Unlike electrical mapping, delivery of current for burning multiple myocardial holes does not absolutely require distinct multiple supply wires. In one embodiment, supply wire 46 slides longitudinally within arm 42 and cutting probe 44 slides radially through an orifice 52 in arm 42. Thus, longitudinally sliding the supply wire causes cutting probe 44 to slide radially toward the heart chamber wall, as indicated by the arrows in FIG. 3. In a preferred embodiment, electrical insulation coats either the exterior of supply wire 46 or the interior of arm lumen 50, or both.

Figure 4:
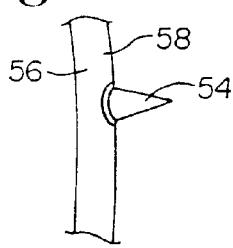
FIG. 4 is fragmentary, side view of a PMR basket cutting probe wherein the probe is an electrode protruding from an insulated arm.

Referring now to FIG. 4, another arm 58 and cutting means is illustrated in FIG. 4 in a cutting electrode 54 having an electrically insulating coating 56 over arm 58, leaving only cutting electrode 54 exposed. The arm embodiment of FIG. 4 allows use of smaller diameter arms as no lumen is required as the insulation is external to the arm. This can allow more arms to be fit within outer tube 26 when retracted. A greater number of arms in the basket allows the formation of a greater number of holes simultaneously formed. In use, after expanding the PMR basket, cutting electrode 54 is brought into close proximity to the heart chamber wall and sufficient electrical potential supplied to a supply wire to burn a hole in the heart chamber wall.

Figure 5:
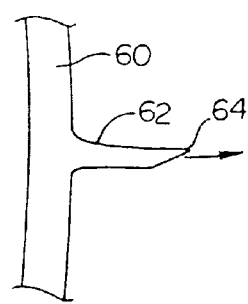
FIG. 5 is fragmentary, side view of a PMR basket cutting probe wherein the probe is a needle having a lumen and a sharp point.

Referring now to FIG. 5, another arm 60 is illustrated, having a cutting needle 62 terminating is a cutting tip 64. In one embodiment, needle 62 is formed of a solid material such as stainless steel. In another embodiment, needle 62 contains a lumen and cutting tip orifice such that a lumen through arm 60 can supply a high pressure fluid through cutting needle 64 and cutting tip 64. Needle 64 can be used in some methods to deliver angiogenic materials in conjunction with the hole formation by cutting tip 64. For example, angiogenic material can be delivered into a hole recently burned by RF current delivered through needle 62. Contrast media may also be delivered through needle 62.

Figure 6:
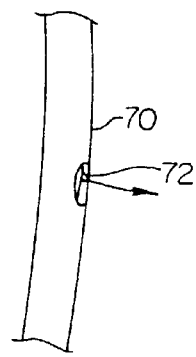
FIG. 6 is fragmentary, side view of a PMR basket arm wherein the cutting means including a water jet orifice supplied by the flexible arm lumen.

Referring now to FIG. 6, another arm 70 is illustrated, having a cutting orifice 72 used to deliver fluid under high pressure to form myocardial holes. Cutting orifice 72 supplies sufficiently high pressure fluid to form holes without requiring the use of electrodes or sharp needles. In use, arm 70 is brought into close contact with a heart chamber wall and high pressure fluid forced through the arm and other arms.

Referring now to FIG. 7, yet another embodiment is illustrated in an arm 74 having a burning electrode 76 protruding from an insulated housing 78. Insulated housing 78 and electrode 76 allow a conventional electrophysiological mapping basket to be converted into a PMR cutting device. Insulating housing 78 can be formed of a material such as Teflon® or other thermoplastic such as PEBA. Burning electrode 76 has a rounded distal tip, to form a crater shaped burn in the heart chamber wall. Other cutting electrodes, in particular, longer and sharper tipped electrodes, can also be used with the embodiment of FIG. 7.

Referring now to FIG. 8, a PMR basket device 80 is illustrated. PMR device 80 includes a basket 82 formed of a plurality of arms 83 terminating in distal portion 92 and proximal portion 94. An outer shaft 84 is slidably disposed over an intermediate shaft 96 which can have an inner, steerable cutting probe 81 disposed within. In one embodiment, intermediate shaft 96 functions as a hub, having arms 83 secured thereto and steerable probe 81 slidably and rotatably received within. Steerable cutting probe 81 includes a shaft 86 preferably having a lumen therethrough. Basket 82 can be similar, in shape and arcuate bias of individual arms, to basket 30 in FIG. 1, but having no means for cutting mounted over the length of the arms. Basket proximal portion 94 is affixed to the distal end of intermediate shaft 96. In one embodiment, as in shaft 96 in FIG. 8, the intermediate shaft is tubular, having cutting probe shaft 86 slidably disposed within.

In another embodiment, the intermediate shaft and cutting probe shaft 86 are both slidably disposed, side-by-side, within outer shaft 84. Cutting probe shaft 86 is preferably arcuately biased and slidably disposed within outer shaft 84 such that the degree of arc exhibited by the probe can be controlled by longitudinally advancing or retracting the arcuately biased member within the constraints of outer shaft 84. Allowing more of cutting probe shaft 86 to extend distally from outer shaft 84 allows more the arcuate shape to be attained. In one embodiment, cutting probe shaft 86 is formed of a shape memory material such as Nitinol. In another embodiment, cutting probe shaft 86 is formed of a spiral wound material such as woven stainless steel braid in a polymer which is biased to have an unconstrained arcuate shape. A cutting wire 90 is preferably slidably disposed within shaft 86 and can terminate in a distal cutting tip 90. In another embodiment, an elastic fabric may be suspended around basket 82 to form a balloon-like enclosure. A plurality of apertures may be formed in the fabric such that cutting tip 88 can exit the basket to access the myocardium only through a hole in the fabric. The hole may be placed in a predetermined array to guide the arrangement of channels or craters to be formed during the PMR procedure.

In use, intermediate shaft 96, basket 82 and cutting probe 81 can be proximally retracted within outer shaft 84 in preparation for placement. The distal end of outer shaft 84 can be advanced over the aorta and into a heart chamber such as the left ventricle. Intermediate shaft 96 can be advanced distally into the left ventricle, forcing basket 82 out from within outer shaft 84. Cutting probe shaft 86 can also be advanced distally from outer shaft 84, either separately or together with basket 82. Basket 82, freed from the constraint of outer shaft 84, can assume the outwardly bowed arcuate shape imparted by arms 83. Further bowing can be achieved by distally pushing intermediate shaft 96, thereby forcing basket distal portion 92 against the ventricle wall near the apex. Basket 82 thus acts as an anchor, stabilizing the position of cutting probe 81 within the ventricle.

In one embodiment, the shape of cutting probe 31 can be controlled in part by imparting to cutting probe shaft 86 an arcuate bias and controlling the length of shaft 86 that is allowed to extend from within outer shaft 84 and inner shaft 96. With the degree of arc thus controlled, cutting wire 90 can be advanced until contact with the heart chamber wall is effected. With cutting tip 88 in contact with the chamber wall, a suitable RF electrical current can be passed through cutting wire 90, thereby burning a hole in the heart chamber wall. Cutting probe 81 can be rotated, allowing a circle or arc of myocardial holes to be formed within the heart chamber. Adjusting the longitudinal position of cutting probe 81 allows other series of holes to be formed. In one embodiment (not requiring illustration), an additional tube is slidably disposed over cutting probe shaft 86, distally past intermediate shaft 94, and within basket 82, allowing control of the arc of cutting probe shaft 86 to be extended longitudinally. While anchoring basket 82 is preferably used in conjunction with electrical PMR cutting means, other cutting means, including sharp cutting tips, are used in other embodiments.

Referring now to FIG. 9, a PMR brush device 100 is illustrated, including an inner shaft 104 having a distal end 105 and a plurality of arcuate electrode wires 106 secured to distal end 105. Inner shaft 104 is slidably disposed within an outer shaft 102. Electrode wires 106 can terminate in a distal cutting tips 108 which, in one embodiment, are formed of metallic balls of platinum or gold brazed to the distal ends of electrode wires 106. In one embodiment, electrode wires 106 are insulated except for cutting tip 108. Electrode wires 106 can be formed of a shape memory material such as Nitinol. The electrodes can be formed into an initial arcuate shape, with the shape being remembered after the electrodes are freed from constraint and warmed to body temperature. Referring now to FIG. 10, inner shaft 104 is illustrated in a retracted position within outer shaft 102.

In use, PMR brush device 100 can be put into a retracted position as illustrated in FIG. 10 and advanced over the aorta and into a heart chamber such as the left ventricle. Outer shaft 102 can be retracted, freeing electrode wires 106 of the restraint of shaft 102, allowing the wires to assume an arcuate shape such that cutting tips 108 can engage the ventricle wall. With cutting tips 108 in position, a suitable electrical source can be switched, causing cutting tips 108 to burn holes into the heart chamber wall. In one embodiment, electrode wires 106 are supplied by a common supply wire and all electrodes fired simultaneously.

PMR brush device 100 can be made to engage the ventricle walls at varying depths within the ventricle. For example, PMR device 100 can have outer shaft 102 only partially retracted, keeping arcuate electrode wires 106 partially straightened and grouped together for engaging the ventricle wall near the apex. After burning a series of holes, outer tube 102 can be retracted further, allowing arcuate electrode wires 106 to splay further apart, allowing a superior, wider portion of the left ventricle to be treated. In one embodiment, electrode wires 106 are preformed to have an extreme arcuate shape such that superior, wide regions of the left ventricle can be treated from a central position in the ventricle. In some methods, brush device 100 may be pulled via inner shaft 104 to more completely treat the right wall of the left ventricle and pushed to more completely treat the left wall of the left ventricle. Upon completion of treatment, electrode wires 106 can be retracted within outer shaft 102 and brush device retracted from the left ventricle.

Figure 11:
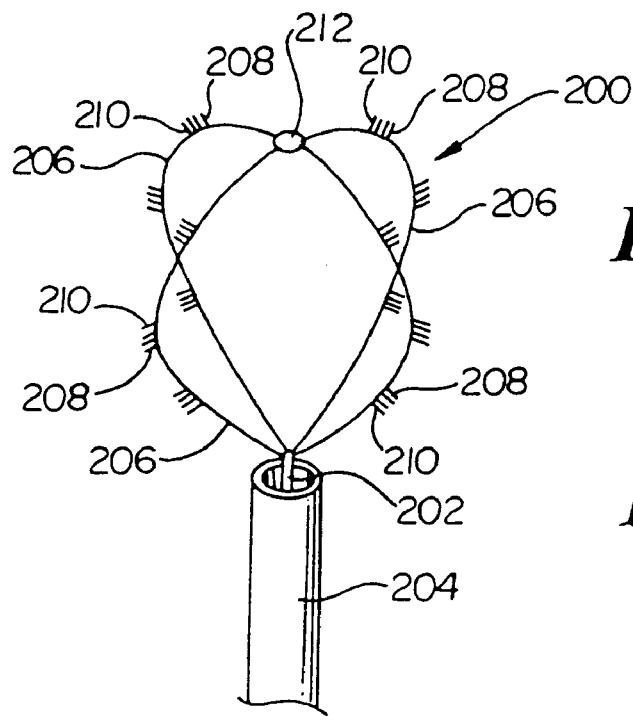
FIG. 11 is the perspective view of a PMR basket having a plurality of electrode groupings disposed thereon.
Figure 12:
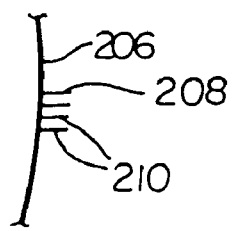
FIG. 12 is a fragmentary view of an electrode grouping from FIG. 11.

FIG. 11 shows yet another embodiment of a PMR basket 200. Basket 200 is disposed at the distal end of an elongate catheter shaft 202 disposed within a guide catheter 204. Basket 200 is formed from a plurality of wires 206 each having proximal ends and distal ends. The distal ends and proximal ends, respectively are connected to each other. Wires 206 are biased to expand basket 200 transversely when unconstrained. Extending generally transversely from wires 206 are a plurality of electrode groupings 208. Each electrode grouping includes a plurality of individual elongate electrodes 210. Each of the individual electrodes 210 preferably has a diameter of about 0.001 inches to 0.009 inches. A radiopaque marker 212 can be disposed at the distal end of basket 200. FIG. 12 is a fragmentary view of an electrode grouping from FIG. 11.

To conduct radiofrequency energy, catheter 202 must include or be formed from a conductor, such as stainless steel or other biocompatible metal. Likewise, wires 206 and electrodes 210 must be formed from a conductor such as stainless steel, Nitinol or other biocompatible material. If wires 206 are formed from Nitinol they can be heat set to expand upon introduction of basket 200 into the left ventricle of the patient. The conductor of catheter 200 and wires 206 should be insulated to concentrate the release of RF energy at electrode groupings 208. Catheter 202 can be insulated by, for example, a surrounding layer of polyethylene, polyimide or PTFE. Wires 206 are preferably insulated by a heat shrink PTFE layer or other biocompatible insulator. Marker 212 can be formed from gold, platinum or other highly radiopaque material. Electrodes 210 can be plated with gold or other radiopaque material to enhance their visibility by fluoroscopy. Each electrode 210 can be insulated in a cylindrical ceramic housing to provide electrical insulation and thermal shielding from wires 206. Each electrode 210 is preferably between about 0.0 to 0.1 inches in length. Electrodes 210 can include a spherically shaped tip having a diameter of about 0.01 to 0.039 inches. Each grouping 208 is preferably spaced about 0.19 to 0.078 apart.

In use, guide catheter 204 is advanced to a chamber of a patients heart, such as a left ventricle. Basket 200 is advanced in a constrained and compressed configuration to the left ventricle. Upon being advanced out of guide catheter 204 into the left ventricle, basket 204 expands. The expanded size of basket 200 should be large enough to bring electrodes 210 in contact with the wall of the left ventricle. RF energy of a sufficient magnitude is then delivered to the heart wall by way of electrodes 210. The small diameter electrodes 210 can deliver a high current density to the tissue. By placing electrodes 210 in groupings 208, the tissue can be cratered, that is a wound can be formed in the tissue which has a width greater than its depth.

Figure 13:
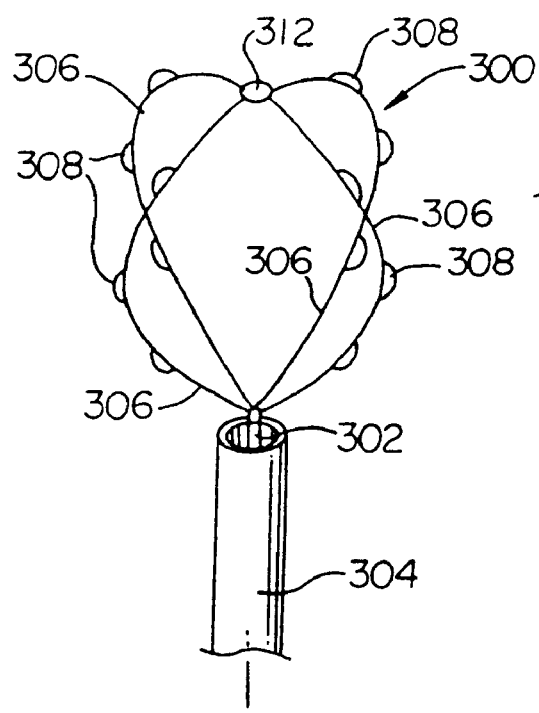
FIG. 13 is a perspective view a PMR basket having a plurality of loop electrodes disposed thereon.
Figure 14:
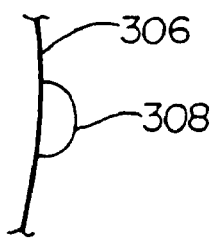
FIG. 14 is a fragmentary view of a loop electrode from FIG. 13.
Figure 18:
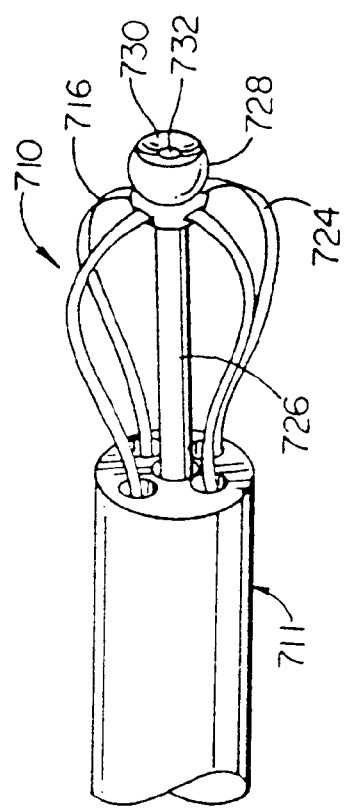
Figure 20:
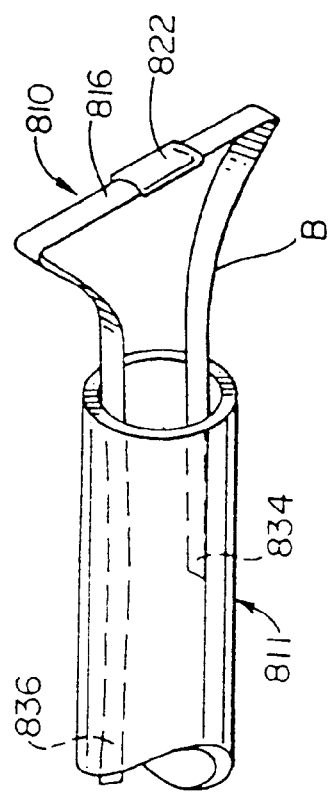
Figure 17:
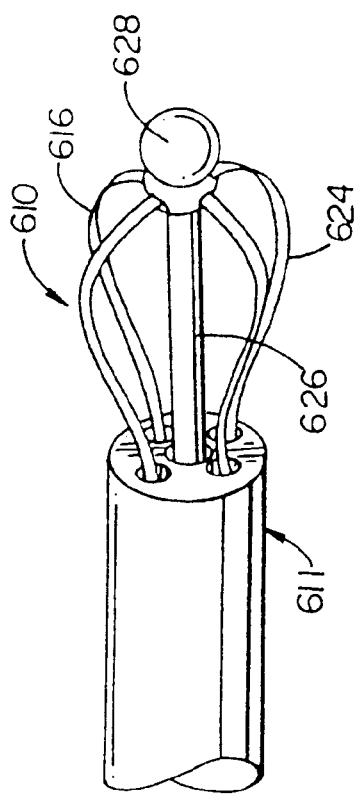
Figure 19:
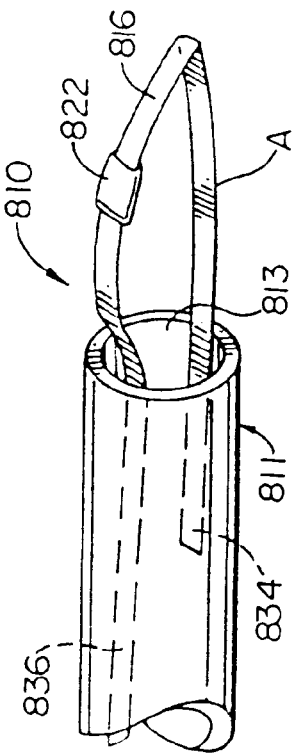

FIG. 13 is a perspective view yet another embodiment of a PMR basket 300. PMR basket 300 is disposed at the distal end of a catheter 302. Basket 300 is advancable to a patient's heart chamber through a guide catheter 304. Basket 300 is formed from a plurality of wires 306 biased to expand basket 300 transversely when unconstrained. Each wire 306 has a distal end and a proximal end, the proximal ends and distal ends of each wire respectively are connected to form basket 300. A plurality of loops 308 are disposed on each wire 306. The wire forming each loop has a diameter of about 0.039 inches to about 0.197 inches. Loops 308 can have a semi-circular configuration. A radiopaque marker 312 can be disposed at the distal end of basket 300. FIG. 14 is a fragmentary view of basket 300 showing a side view of a loop 308 on wire 306. Each loop 308 is preferably contained within a cylindrical ceramic housing to provide electrical isolation and thermal shielding from wires 306.

The various elements of the basket embodiment of FIGS. 13 and 14 can be formed from the materials cited above in connection with the embodiment of FIGS. 11 and 12. Basket 300 is intended to be used in essentially the same manner as basket 200 to form craters in the myocardium of a patient's heart.

If can be appreciated that each of the devices disclosed herein could be made bi-polar rather than mono-polar as shown. To make these devices bi-polar, a ground electrode can be disposed proximate the electrodes shown.

Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The inventions's scope is, of course, defined in the language in which the appended claims are expressed.

What is claimed is:

1. A PMR device for forming a plurality of holes in a heart chamber wall comprising:
   an elongate tubular shaft having a longitudinal axis, a proximal end and a distal end;
   a basket, said basket being expandable and collapsible and including a plurality of arms;

means for expanding and collapsing said basket;

a plurality of cutting means carried on said arms and disposed outward relative to said longitudinal axis, such that said plurality of holes can be formed in said heart chamber wall by expanding said basket, causing said cutting means to be brought into close proximity with said heart chamber wall.

2. A medical device as recited in claim 1, wherein said shaft has a lumen, further comprising means for advancing said basket through said shaft lumen and out said shaft distal end.

3. A medical device as recited in claim 2, wherein said basket is biased to expand upon being advanced from said shaft distal end.

4. A medical device as recited in claim 3, wherein said cutting means are electrodes.

5. The device in accordance with claim 4, wherein said electrodes are disposed in a plurality of groupings.

6. A device in accordance with claim 5, wherein each grouping includes at least three electrodes.

7. The device in accordance with claim 5, wherein said electrodes are generally elongate.

8. The device in accordance with claim 7, wherein said electrodes have a width of about 0.001 inches to about 0.009 inches.

9. The device in accordance with claim 4, wherein said electrodes have a loop shape.

10. The device in accordance with claim 9, wherein the loop shape is generally semi-circular.

11. The device in accordance with claim 9, wherein at least one of the electrodes includes a wire having a diameter of about 0.04 inches to about 0.2 inches.

12. A PMR basket for forming a plurality of holes in a heart chamber wall comprising:

a plurality of elongate flexible arms each having a longitudinal axis, a distal end and a proximal end, said elongate arms being secured together at said distal ends and said proximal ends, said arms being biased so as to bow outward relative to an axis through said secured distal and proximal ends, said flexible arms carrying a plurality of cutting means disposed outward relative to said axis through said arm distal and proximal ends, such that said plurality of holes can be formed in said heart chamber wall by allowing said biased flexible arms carrying said cutting means to bow outward against said heart chamber walls.

13. A PMR basket as recited in claim 12, wherein said cutting means are electrodes protruding outward from said flexible arms and said flexible arms include means for delivering radio frequency current to said electrodes.

14. A PMR basket as recited in claim 13, wherein said flexible arms have insulated conducting wires disposed within said arms, said wires being in electrical communication with said electrodes.

15. The device in accordance with claim 14, wherein said electrodes are disposed in a plurality of groupings.

16. A device in accordance with claim 15, wherein each grouping includes at least three electrodes.

17. The device in accordance with claim 15, wherein said electrodes are generally elongate.

18. The device in accordance with claim 17, wherein said electrodes have a width of about 0.001 inches to about 0.009 inches.

19. The device in accordance with claim 14, wherein said electrodes have a loop shape.

20. The device in accordance with claim 19, wherein the loop shape is generally semi-circular.

21. The device in accordance with claim 19, wherein at least one of the electrodes includes a wire having a diameter of about 0.04 inches to about 0.2 inches.

22. A PMR basket as recited in claim 12, wherein said cutting means are needles.

* * * * *